US008158678B2

(12) United States Patent
Bonda et al.

(10) Patent No.: US 8,158,678 B2
(45) Date of Patent: Apr. 17, 2012

(54) PHOTOABSORBING, HIGHLY CONJUGATED COMPOUNDS OF CYANOACRYLIC ESTERS, SUNSCREEN COMPOSITIONS AND METHODS OF USE

(75) Inventors: Craig A. Bonda, Winfield, IL (US); Anna Pavlovic, Elmwood Park, IL (US)

(73) Assignee: CPH Innovations Corp.

( * ) Notice: Subject to any disclaimer, the term of this patent is extended or adjusted under 35 U.S.C. 154(b) by 979 days.

(21) Appl. No.: 11/101,214

(22) Filed: Apr. 7, 2005

(65) Prior Publication Data
US 2006/0228311 A1 Oct. 12, 2006

(51) Int. Cl.
| A01N 37/34 | (2006.01) |
| A01N 37/36 | (2006.01) |
| A01N 37/40 | (2006.01) |
| A61K 31/275 | (2006.01) |
| A61K 31/277 | (2006.01) |
| A01N 37/00 | (2006.01) |
| A01N 37/38 | (2006.01) |
| A61K 31/00 | (2006.01) |
| A61K 31/28 | (2006.01) |

(52) U.S. Cl. ......... 514/520; 514/521; 514/523; 514/525
(58) Field of Classification Search .................. 514/520, 514/521, 523, 525
See application file for complete search history.

(56) References Cited

U.S. PATENT DOCUMENTS

| 2,839,402 A | 6/1958 | Edwards et al. ............... 131/332 |
| 3,215,724 A * | 11/1965 | Strobel et al. ................. 558/402 |
| 3,215,725 A | 11/1965 | Strobel et al. ................. 260/465 |
| 3,272,855 A | 9/1966 | Strobel et al. ................. 260/465 |
| 3,275,520 A * | 9/1966 | Strobel et al. ................... 424/59 |
| 3,337,357 A | 8/1967 | Strobel et al. ................. 106/178 |
| 3,445,545 A | 5/1969 | Skoultchi ...................... 260/881 |
| 3,461,108 A | 8/1969 | Heilman et al. ............. 260/78.5 |
| 3,560,455 A | 2/1971 | Hazen et al. .................. 526/272 |
| 3,560,456 A | 2/1971 | Hazen et al. .................. 526/272 |
| 3,560,457 A | 2/1971 | Hazen et al. .................. 526/272 |
| 3,580,893 A | 5/1971 | Heilman ...................... 525/384 |
| 3,706,704 A | 12/1972 | Heilman ...................... 526/208 |
| 3,729,450 A | 4/1973 | Galiano et al. ............... 528/500 |
| 3,729,451 A | 4/1973 | Blecke et al. ............... 260/78.5 |
| 3,860,700 A | 1/1975 | Viout et al. ..................... 424/61 |
| RE28,475 E | 7/1975 | Blecke et al. ............... 260/78.5 |
| 3,992,356 A | 11/1976 | Jacquet et al. .................. 260/47 |
| 4,069,046 A | 1/1978 | Hoegl et al. ...................... 96/1 |
| 4,107,290 A | 8/1978 | Jacquet et al. .................. 424/47 |
| 4,128,536 A | 12/1978 | Brodsky et al. ................ 427/54 |
| 4,178,303 A | 12/1979 | Lorenz et al. ................. 260/465 |
| 4,202,834 A | 5/1980 | Gruber et al. ................. 260/465 |
| 4,202,836 A | 5/1980 | Gruber et al. ............... 260/465.4 |
| 4,203,919 A | 5/1980 | Gruber et al. ................. 260/465 |
| 4,207,253 A | 6/1980 | Lorenz et al. ................. 260/465 |
| 4,218,392 A | 8/1980 | Lorenz et al. ................. 260/465 |
| 4,247,475 A | 1/1981 | Ching .......................... 260/465 |
| 4,260,719 A | 4/1981 | Ching .......................... 528/196 |
| 4,263,366 A | 4/1981 | Lorenz et al. ................. 428/332 |
| 4,264,680 A | 4/1981 | Anthony ....................... 428/412 |
| 4,276,136 A | 6/1981 | Gruber et al. ................. 204/159 |
| 4,387,089 A | 6/1983 | De Polo ........................... 424/59 |
| 4,489,057 A | 12/1984 | Welters et al. ................... 424/47 |
| 4,562,067 A | 12/1985 | Hopp et al. ..................... 424/59 |
| 4,868,246 A | 9/1989 | MacLeay et al. ............. 525/142 |
| 5,013,777 A | 5/1991 | MacLeay et al. ............. 524/159 |
| 5,096,977 A | 3/1992 | MacLeay et al. ............. 525/343 |
| 5,210,275 A | 5/1993 | Sabatelli ........................ 560/43 |
| 5,321,112 A | 6/1994 | Olson ............................. 528/75 |
| 5,576,354 A | 11/1996 | Deflandre et al. ............. 514/685 |
| 5,681,871 A | 10/1997 | Molock et al. ................. 523/106 |
| 5,821,380 A | 10/1998 | Holderbaum et al. ......... 558/443 |
| 5,869,099 A | 2/1999 | Keller et al. .................. 424/486 |
| 5,882,633 A | 3/1999 | Pisson et al. .................... 424/59 |
| 5,972,324 A | 10/1999 | Zofchak et al. ............. 424/78.03 |
| 5,989,528 A * | 11/1999 | Tanner et al. ................... 424/59 |
| 5,993,789 A | 11/1999 | Bonda et al. .................... 424/59 |
| 6,001,337 A | 12/1999 | Keller et al. .................... 424/59 |
| 6,033,649 A | 3/2000 | Gonzenbach et al. ........... 424/60 |
| 6,126,925 A | 10/2000 | Bonda et al. .................... 424/59 |
| 6,143,850 A | 11/2000 | Keller et al. .................. 526/304 |
| 6,224,854 B1 | 5/2001 | Robinson ....................... 424/59 |
| 6,284,916 B1 | 9/2001 | Bonda et al. .................... 560/80 |
| 6,297,300 B1 | 10/2001 | Van Nuffel ..................... 524/91 |
| 6,306,507 B1 | 10/2001 | Brunelle et al. ............. 428/423.7 |
| 6,358,892 B1 | 3/2002 | Harrison et al. .............. 508/192 |

(Continued)

FOREIGN PATENT DOCUMENTS

CA 1 164 886 4/1984

(Continued)

OTHER PUBLICATIONS

International Search Report dated Nov. 16, 2006, International application No. PCT/US2006/010958.
Written Opinion of the International Searching Authority, International application No. PCT/US2006/010958.
"Photostability of HallStar Photostable SPF 32 Sunscreen Compared to Neutrogena UVA/UVB Sunblock SPF 30," Suncare Research Laboratories, Memphis, Tennessee (Oct. 5, 2000).
Beckwith, in "The chemistry of amides: Synthesis of amides," Zabicky, J., Ed. Interscience: New York, pp. 73-185 (1970).

(Continued)

*Primary Examiner* — Fereydoun G Sajjadi
*Assistant Examiner* — Courtney Brown
(74) *Attorney, Agent, or Firm* — Marshall, Gerstein & Borun LLP

(57) ABSTRACT

Novel derivatives of α-cyano-β-naphthyl acrylates, sunscreen compositions including one or more α-cyano-β-naphthyl acrylate derivatives are described herein. Also disclosed are methods for stabilizing a sunscreen composition and methods of filtering out ultra-violet light from a substrate by the addition of one or more of the foregoing α-cyano-β-naphthyl acrylate derivatives.

5 Claims, 5 Drawing Sheets

U.S. PATENT DOCUMENTS

| | | | |
|---|---|---|---|
| 6,365,311 B1 | 4/2002 | Wilson et al. | 430/108.2 |
| 6,416,773 B2 | 7/2002 | Heidenfelder et al. | 424/401 |
| 6,441,071 B1 | 8/2002 | Van Nuffel | 524/316 |
| 6,485,713 B1 | 11/2002 | Bonda et al. | 424/59 |
| 6,491,901 B2 | 12/2002 | Gers-barlag et al. | 424/59 |
| 6,538,161 B2 | 3/2003 | Nakaya et al. | 568/424 |
| 6,544,305 B2 | 4/2003 | Wood et al. | 44/275 |
| 6,610,409 B2 | 8/2003 | Pickett et al. | 428/423.7 |
| 6,689,474 B2 | 2/2004 | Pickett et al. | 428/423.7 |
| 6,861,460 B2 | 3/2005 | Gorny et al. | 524/318 |
| 2001/0022966 A1 | 9/2001 | Gers-barlag et al. | 424/59 |
| 2002/0194777 A1 | 12/2002 | Wood et al. | 44/275 |
| 2003/0000130 A1 | 1/2003 | Wood et al. | 44/275 |
| 2003/0069338 A1 | 4/2003 | Goossens et al. | 524/186 |
| 2003/0072945 A1 | 4/2003 | Pickett et al. | 428/412 |
| 2003/0130390 A1 | 7/2003 | Gorny et al. | 524/307 |
| 2003/0180542 A1 | 9/2003 | Pickett et al. | 428/423.7 |
| 2004/0057912 A1 | 3/2004 | Bonda et al. | 424/59 |
| 2005/0025727 A1 | 2/2005 | Lott | 424/59 |

FOREIGN PATENT DOCUMENTS

| | | |
|---|---|---|
| CA | 2204430 | 5/1996 |
| DE | 31 06 071 | 2/1982 |
| DE | 44 40 055 | 5/1996 |
| DE | 195 19 895 | 12/1996 |
| DE | 196 30 479 | 1/1998 |
| DE | 100 08 895 | 8/2001 |
| DE | 100 15 863 | 10/2001 |
| DE | 100 26 628 | 12/2001 |
| DE | 100 58 290 | 5/2002 |
| EP | 0 675 875 | 11/1998 |
| EP | 0 900 782 | 3/1999 |
| EP | 1 129 696 | 9/2001 |
| EP | 1 308 084 | 5/2003 |
| GB | 1129029 | 10/1968 |
| JP | 52-133959 | 11/1977 |
| JP | 52-133960 | 11/1977 |
| JP | 52-133961 | 11/1977 |
| JP | 52-133962 | 11/1977 |
| JP | 52-156843 | 12/1977 |
| JP | 53-007655 | 1/1978 |
| JP | 53-007656 | 1/1978 |
| JP | 54-005940 | 1/1979 |
| JP | 54-154532 | 12/1979 |
| JP | 56-140959 | 4/1981 |
| JP | 7-285924 | 10/1995 |
| JP | 7-325421 | 12/1995 |
| JP | 7-330637 | 12/1995 |
| JP | 7-330734 | 12/1995 |
| JP | 7-333871 | 12/1995 |
| JP | 8-050362 | 2/1996 |
| JP | 8-059520 | 3/1996 |
| JP | 8-245513 | 9/1996 |
| JP | 8-245518 | 9/1996 |
| JP | 8-248655 | 9/1996 |
| JP | 8-262759 | 10/1996 |
| JP | 9-288366 | 11/1997 |
| JP | 9-319104 | 12/1997 |
| JP | 9-319110 | 12/1997 |
| JP | 11-143095 | 5/1999 |
| JP | 2004-243596 | 9/2004 |
| WO | WO 94/14760 | 7/1994 |
| WO | WO 96/15102 | 5/1996 |
| WO | WO 00/44340 | 8/2000 |
| WO | WO 01/16224 | 3/2001 |
| WO | WO 01/57125 | 8/2001 |
| WO | WO 01/90233 | 11/2001 |
| WO | WO 01/92395 | 12/2001 |
| WO | WO 02/42368 | 5/2002 |
| WO | WO 2004/031294 | 4/2004 |
| WO | WO 2004/099150 | 11/2004 |

OTHER PUBLICATIONS

Bentley et al., "Medium Effects on the Rates and Mechanisms of Solvolytic Reactions," *Adv. Phys. Org. Chem.*, vol. 14, pp. 1-67 (1977).

Bentley et al., "$Y_x$ Scales of Solvent Ionizing Power," *Progr. Phys. Org. Chem.*, vol. 17, pp. 121-158 (1990).

Bettencourt et al., "Kinetics of proton transfer from phosphonium ions to electrogenerated bases: polar, steric and structural influences on kinetic acidity and basicity" *J. Chem. Soc., Perkin Trans.* 2, pp. 515-522 (1998).

Bhattacharyya et al., "Steroselective synthesis of A/B-octahydrophenanthrene skeleton related to diterpenes via reductive alkylation in anhydrous ammonia," Tetrahedron Lett., vol. 23(40), pp. 4175-4176 (1982).

Das et al., "Stereocontrolled total synthesis of (±)-totaryl methyl ether and (±)-semperviryl methyl ether," Tetrahedron, vol. 48(41), pp. 9101-9110 (1992).

Dimroth et al., Über Pyridinium-N-Phenol-Betaine Und Ihre Verwendung Zur Charakterisierung Der Polarität Von Lösungsmitteln *Justus Liebigs Ann. Chem.*, vol. 661 pp. 1-37 (1963).

Diurno et al., "Reaction products of indandione with ethyl α-cyano-β-arylacrylates," Bollettino—Societa Italiana di Biologia Sperimentale, vol. 60(1), pp. 79-84 (1984).

Fainberg et al., "Correlation of Solvolysis Rates. III. t-Butyl Chloride in a Wide Range of Solvent Mixtures," *J. Am Chem. Soc.*, vol. 78 pp. 2770-2777 (1956).

Foucaud et al., "Comptes Rendus Hebdomadaires Des Seances De L'Academie Des Sciences," Compt. Rend., vol. 267(8), pp. 1538-1540 (1963).

Foucaud, "Preparation of α-methyl-α-(1-naphthyl)succinic acid," Compt. Rend., vol. 254, pp. 1301-1302 (1962).

Gerngross et al., "Synthesis of benzylideneglycine ethyl ester. Stability of the azomethine group in Schiff bases," Chem. Ber., vol. 96(10), pp. 2550-2555 (1963).

Ghosh et al., "Benzopyrans. Part 32. Reaction of some simple condensates of 4-oxo-4H-1-benzopyran-3-carboxaldehydes with diazomethane—synthesis of heterocycles linked to 3-position of [1]benzopyran," Indian Journal of Chemistry, Section B: Organic Chemistry including Medicinal Chemistry, vol. 32B(6), pp. 630-636 (1993).

Grunwald et al., "The Correlation of Solvolysis Rates," J. Am. Chem. Soc., vol. 70, pp. 846-854 (1948).

Haslem, "Recent Developments in Methods for the Esterification and Protection of the Carboxyl Group," *Tetrahedron*, vol. 36, pp. 2409-2433 (1980).

Hirata et al. "Mass spectra of α-β-substituted phenyl crotonates. II. Fragmentation of ethyl α-cyano-β-2,4-disubstituted phenyl crotonates and ethyl α-cyano-β-naphthyl crotonates," Nagoya Kogyo Daigaku Gakuho, vol. 27, pp. 169-175 (1975).

Kametani et al., "Studies on the Syntheses of Heterocyclic Compounds/ DCCXL. Studies on the Syntheses of Analgesics. XLIX. Studies on the Synthesis of 2-(6-Methoxy-2-Naphthyl) Proprionic Acid," Yakugaku Zasshi, vol. 98(2), pp. 146-152 (1978).

Kamlet et al., "An Examination of Linear Solvation Energy Relationships," *Progr. Phys. Org. Chem.*, vol. 13, pp. 485-630 (1981).

Katritzky et al., "Synthesis of 3,3'-Diarylpyrrolidines from Diaryl Ketones," Center for Heterocyclic Compounds, published online at http://www.arkat-usa.org/zark/journal/2003/GB-594J/594J.pdf, (Gainesville, FL), 5 pages (2003).

Kosower, "The Effect of Solvent on Spectra. I. A New Empirical Measure of Solvent Polarity Z-Values," *J. Am Chem. Soc.*, vol. 80, pp. 3253-3260 (1958).

Latif et al., "Carbonyl and thiocarbonyl compounds. IX. Synthesis of benzoxanthene ethers by the action of tetrahalo-o-benzoquinones," Canadian Journal of Chemistry, vol. 43(5), pp. 1246-1249 (1965).

Lehnert, Knoevenagel-Kondensationen Mit TiCl$_4$/BASE-III[1] Tetrahedron vol. 29, pp. 635-638 (1973).

McNaught et al., "IUPAC Compendium of Chemical Terminology," 2$^{nd}$ Ed. (1997).

Moal et al, "Structure and physicochemical properties of compounds with active ethylenic bonds. I. Synthesis and structure of β,β-disubstituted α-cyanoacrylic esters," Bulletin de la Societe Chimique de France, vol. 3, pp. 1033-1040 (1966).

Mustafa et al., "3,4-Benzoxanthene cyclic ethers." Receuil des Travaux Chimiques des Pays-Bas, vol. 84(11), pp. 1386-1398 (1965).

Nagai, "Stereochemistry of ethyl α-cyano-β-methyl-β-(1-naphthyl)acrylate and ethyl α-cyano-β-methyl-4-bromo-2-nitrocinnamate," Nippon Kagaku Zasshi, vol. 91(4), pp. 362-370 (1970).

Nagai, "Ultraviolet spectral studies on ethyl α-cyano-β-(1- and 2-naphyl)acrylates," Nagoya Kogyo Daigaku Gakuho, vol. 22, pp. 143-149 (1970).

Reichardt, "Solvents and Solvent Effects in Organic Chemistry," 2nd Ed., Chap. 7: Empirical Parameters of Solvent Polarity, VCH Publishers, New York, New York (1998).

Robert et al., "Epoxides α,α-disubstituted with electron attracting goups. II. Sterochemistry and epoxidation mechanism of ethyl α-cyanoacrylates with sodium hypochlorite," Bulletin de la Societe Chimique de France, vol. 7, pp. 2531-2537 (1969).

Sayre et al., "Photostability Testing of Avobenzone," Allured's Cosmetics & Toiletries Magazine, vol. 114, No. 5, pp. 85-91 (May 1999).

Tarras-Wahlberg et al., "Changes in Ultraviolet Absorption of Sunscreens After Ultraviolet Radiation," *J. Investigative Dermatology*, vol. 113, No. 4, pp. 547-553 (1999).

Turro, *Modern Molecular Photochemistry* Benjamin/Cummings Publ. Co., Menlo Park, California, pp. 296-361 (1991).

Wittig et al., "zur Umkehrbarkeit von Kondensationsrektionen in alkalischen Medium", Chemische Berichte, p. 117, lines 13-21, vol. 83(1950).

* cited by examiner

US 8,158,678 B2

PHOTOABSORBING, HIGHLY CONJUGATED COMPOUNDS OF CYANOACRYLIC ESTERS, SUNSCREEN COMPOSITIONS AND METHODS OF USE

BACKGROUND

1. Field of the Technology

The present invention relates to new photoactive α-cyano-β-naphthyl acrylate derivatives, sunscreen compositions containing one or more of these compounds, methods to increase the photostability of sunscreen compositions by incorporating one or more of these new compounds therein, and methods of protecting a surface using a sunscreen composition containing one or more of these new photoactive compounds.

2. Brief Description of the Related Technology

It is well known that ultraviolet radiation (light) having a wavelength from about 280 nm or 290 nm to about 320 nm (UV-B) is harmful to human skin, causing burns that are detrimental to the development of a good sun tan. UV-A radiation (about 320 nm to about 400 nm), while producing tanning of the skin, also can cause damage, particularly to very lightly colored or sensitive skin, leading to reduction of skin elasticity and wrinkles. Therefore, a sunscreen composition for use on human skin preferably includes both a UV-A and a UV-B filter to prevent most of the sunlight within the full range of about 280 nm or 290 nm to about 400 nm from damaging human skin.

Ultraviolet radiation from the sun or artificial sources can also cause harm to coatings containing photoactive substances, such as photoactive pigments and dyes, by breaking down chemical bonds in the structure of a component such as a polymer, a pigment, or a dye. This photodegradation can lead to color fading, loss of gloss, and loss of physical and protective properties of a coating. Photodegradation can take place in several steps which include one or more components of a coating absorbing UV radiation. The absorbed radiation can excite the absorbing molecules and raise them to a higher energy level, which can be very reactive. If the molecule cannot be relaxed, bond cleavage and the formation of free radicals will occur. These free radicals can attack one or more color molecules and/or a polymer backbone and form more free radicals. UV-A and UV-B filters can also be used to absorb UV radiation to protect a pigmented coating.

The UV-B filters that are most widely used in the U.S. in commercial sunscreen compositions are paramethoxycinnamic acid esters, such as 2-ethylhexyl paramethoxycinnamate, commonly referred to as octyl methoxycinnamate or PARSOL MCX, octyl salicylate, benzophenone-3, and oxybenzone.

The organic UV-A filters most commonly used in commercial sunscreen compositions are the dibenzoylmethane derivatives, particularly 4-(1,1 dimethylethyl)-4' methoxydibenzoylmethane (also called avobenzone, sold under the brand name PARSOL 1789). Other dibenzoylmethane derivatives described as UV-A filters are disclosed in U.S. Pat. Nos. 4,489,057, 4,387,089 and 4,562,067, the disclosures of which are hereby incorporated herein by reference. It is also well known that the above described UV-A filters, particularly the dibenzoylmethane derivatives, can suffer from rapid photochemical degradation, when used alone or when combined with the above described most commercially used UV-B filters.

Typically, the above described UV-B filters are combined with the above described UV-A filters and other photoactive compounds and stabilizers in a solution with other lipophilic or oily ingredients. This solution of oily ingredients, known to formulators of cosmetic products including sunscreens as the "oil phase," is typically, but not necessarily, dispersed with the help of emulsifiers and stabilizers into an aqueous solution composed primarily of water, to make an emulsion which becomes a final cream or lotion form of a sunscreen composition, that can then be applied to a surface in a protective film.

The performance of a photoactive compound or a combination of photoactive compounds in a sunscreen composition has been extremely difficult to predict based on the levels of photoactive compounds in the formulation, particularly when the formulation includes one or more photoactive compounds that suffer from relatively rapid photodegradation, such as avobenzone. Because of this, each formulation has required expensive laboratory testing to determine the UV absorbance, as a function of time (quantity) of exposure of the formulation to UV radiation. Moreover, a particularly difficult problem is presented when one photoactive compound in a sunscreen composition acts to increase the rate of photodegradation of another photoactive compound in the composition. This can be accomplished in a number or ways, including a bimolecular reaction between two photoactive compounds and a lowering of the threshold energy need to raise a photoactive compound to its excited state. For example, when avobenzone is combined with octyl methoxycinnamate a bimolecular pathway leads to the rapid photodegradation of both the dibenzoylmethane derivative and the octyl methoxycinnamate.

A typical sunscreen composition includes one or more photoactive compounds, wherein a photoactive compound acts to absorb UV radiation and thereby protect human skin from the harmful effects of UV radiation. The absorption process causes a photoactive compound to reach an excited state, wherein the excited state is characterized by the presence of excited energy (e.g., singlet energy or triplet energy), as compared to the ground state of the photoactive compound. Once a photoactive compound reaches an excited state there exists a number of pathways by which the excited photoactive compound can dissipate its excess energy (e.g., triplet energy), however, many of those pathways adversely affect the ability of the photoactive compound to further absorb UV radiation.

Methods and compositions for stabilizing photoactive compounds, such as dibenzoylmethane derivatives with the use of diesters and/or a polyesters of naphthalene dicarboxylic acid are described in U.S. Pat. Nos. 5,993,789, and 6,284,916, the disclosures of which are hereby incorporated herein by reference. Other methods of stabilizing a dibenzoylmethane derivative include the addition of an α-cyano-diphenylacrylate compound to a sunscreen composition including a dibenzoylmethane derivative. See, Deflandre et al, U.S. Pat. No. 5,576,354 and Gonzenbach et al., U.S. Pat. No. 6,033, 649.

SUMMARY

One aspect of the compounds, compositions, and methods described herein are novel derivatives of α-cyano-β-naphthyl acrylate.

Another aspect of the compounds, compositions, and methods described herein is sunscreen compositions that include a derivative of α-cyano-β-naphthyl acrylate.

Another aspect of the compounds, compositions, and methods described herein is a method of protecting a surface from photodegradation by applying to the surface a composition including a derivative of α-cyano-β-naphthyl acrylate.

Yet another aspect of the compounds, compositions, and methods described herein is a method of protecting a photodegradable material against photodegradation by applying a derivative of α-cyano-β-naphthyl acrylate thereto.

DETAILED DESCRIPTION OF THE PREFERRED EMBODIMENTS

Figure 1:
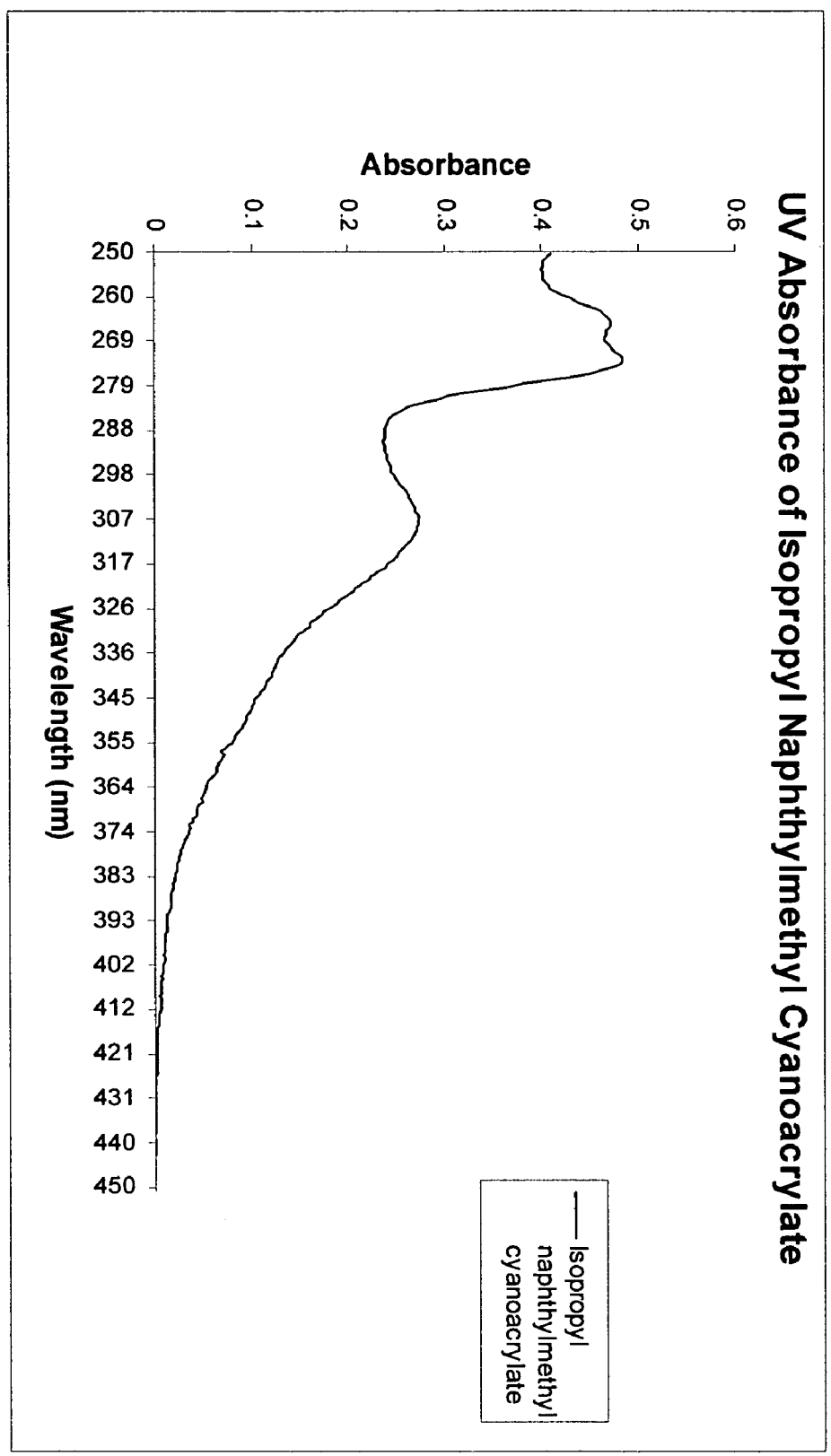
FIG. 1 is a graph of the UV absorbance of isopropyl naphthylmethyl cyanoacrylate of UV light having a wavelength of 250 nm to 450 nm.

A new class of UV absorbing compounds that are highly conjugated are described herein. Further described herein are compounds, compositions, and methods that include a derivative of cyanoacrylate, and in particular, derivatives of α-cyano-β-naphthyl acrylate.

The compounds, compositions, and methods described herein include a highly conjugated α-cyano-β-naphthyl acrylate that absorbs UV radiation and also photostabilizes other UV absorbing compounds in a sunscreen composition.

A photoactive compound is one that responds to light photoelectrically, for example, photoactive compounds that respond to UV radiation photoelectrically by rapid photodegradation. Compounds can exhibit varying levels of UV absorbance depending upon their structure and electronic properties. The stability of a given photoactive compound may also relate to its structure and electronic properties. Photostability is a potential problem with all UV-absorbing compounds (filters) when combined with other UV absorbing molecules, since interactions between multiple UV absorbing compounds can cause one or more UV absorbing compounds in a composition to become unstable.

Disclosed herein are compounds, compositions and methods related to α-cyano-β-naphthyl acrylate compounds which have the formula of structure (I) shown below:

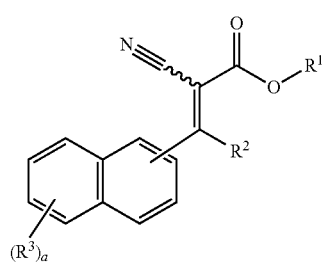

I wherein $R^1$ is selected from the group consisting of $C_3$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; $R^2$ is selected from the group consisting of $C_2$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; $R^3$ is selected from the group consisting of hydroxyl, alkyl, alkenyl, alkynyl, alkoxy, halo, nitro, nitroso, alkylcarbonyl, alkoxycarbonyl, amino, substituted amino, amido, substituted amido, sulfate, carboxylate, oxycarbonyl, cycloalkyl, haloalkyl, cyano, and thioether, and a is in the range of 0 to 7.

The term "alkyl" as used herein refers to straight- and branched-chain hydrocarbon groups, preferably containing one to thirty carbon atoms. Examples of alkyl groups are $C_1$-$C_4$ alkyl groups. As used herein the designation $C_x$-$C_y$, wherein x and y are integers, denotes a group having from x to y carbon atoms, e.g., a $C_1$-$C_4$ alkyl group is an alkyl group having one to four carbon atoms. Nonlimiting examples of alkyl groups include, methyl, ethyl, n-propyl, isopropyl, n-butyl, sec-butyl(2-methylpropyl), and t-butyl(1,1-dimethylethyl).

The term "cycloalkyl" as used herein refers to an aliphatic cyclic hydrocarbon group, preferably containing three to eight carbon atoms. Nonlimiting examples of cycloalkyl groups include cyclopropyl, cyclobutyl, cyclopentyl, and cyclohexyl.

The terms "substituted alkyl" and "substituted cycloalkyl" as used herein refer to an alkyl or cycloalkyl groups having one or more substituents. The substituents can include, but are not limited to, cycloalkyl, aryl, heteroaryl, heterocycloalkyl, substituted aryl, substituted heteroaryl, and substituted heterocycloalkyl. The preferred substituted alkyl groups have one to twenty carbon atoms, not including carbon atoms of the substituent group. Preferably, a substituted alkyl group is mono- or di-substituted at one, two, or three carbon atoms. The substituents can be bound to the same carbon or different carbon atoms.

As used herein, the term "alkenyl" is defined identically as "alkyl," except for containing a carbon-carbon double bond. The term "cycloalkenyl" is identical to "cycloalkyl" except containing a carbon-carbon double bond, e.g., cyclopropenyl, cyclobutenyl, cyclohexenyl, and cyclopentenyl.

The term "aryl" as used herein refers to monocyclic, fused bicyclic, and fused tricyclic carbocyclic aromatic ring systems including, but not limited to, phenyl, naphthyl, tetrahydronaphthyl, phenanthrenyl, biphenylenyl, indanyl, indenyl, anthracenyl, and fluorenyl.

The term "heteroaryl" as used herein refers to monocyclic, fused bicyclic, and fused tricyclic aromatic ring systems, wherein one to four-ring atoms are selected from the group consisting of oxygen, nitrogen, and sulfur, and the remaining ring atoms are carbon, said ring system being joined to the remainder of the molecule by any of the ring atoms. Nonlimiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, thiophenyl, furanyl, quinolinyl, isoquinolinyl, benzoxazolyl, benzimidazolyl, and benzothiazolyl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The terms "substituted aryl," "substituted heteroaryl," and "substituted heterocycloalkyl" as used herein refer to an aryl, heteroaryl, or heterocycloalkyl group substituted by a replacement of one, two, or three of the hydrogen atoms thereon with a substitute such as halo, OR, $N(R)_2$, $C(=O)N(R)_2$, CN, nitro, nitroso, alkylcarbonyl, alkoxycarbonyl, carboxylate, alkyl, substituted alkyl, aryl, substituted aryl, heteroaryl, substituted heteroaryl, cycloalkyl, substituted cycloalkyl, heterocycloalkyl, substituted heterocycloalkyl, $O(CH_2)_{1-3}N(R)_2$, $O(CH_2)_{1-3}CO_2H$, and trifluoromethyl.

The term "polyether" as used herein refers to an alkyl or substituted alkyl in which one or more of the carbon atoms is replaced by an oxygen. Nonlimiting examples of a polyether include methoxymethyl, benzyloxymethyl, ethoxymethyl, and ethoxymethoxyethyl.

The term "alkoxy" as used herein is defined as —OR, wherein R is alkyl, substituted alkyl, aryl, substituted aryl, alkenyl, or substituted alkenyl.

The term "halo" as used herein refers to chlorine, fluorine, bromine, or iodine.

The term "nitro" as used herein is defined as —$NO_2$.

The term "nitroso" as used herein is defined as —NO.

The term "alkylcarbonyl" as used herein is defined as —C(=O)R wherein R is alkyl, alkenyl, alkynyl, aryl, heteroaryl, substituted alkyl, substituted alkenyl, substituted alkynyl, substituted aryl or substituted heteroaryl.

The term "alkoxycarbonyl" as used herein is defined as —C(=O)OR wherein R is alkyl, alkenyl, alkynyl, aryl, heteroaryl, substituted alkyl, substituted alkenyl, substituted alkynyl, substituted aryl or substituted heteroaryl.

The term "amino" as used herein is defined as —$NH_2$, —NHR, or —$NR_2$, wherein R is alkyl, alkenyl, alkynyl, aryl, heteroaryl, substituted alkyl, substituted alkenyl, substituted alkynyl, substituted aryl or substituted heteroaryl.

The term "amido" as used herein is defined as —NHC(=O)R or —NRC(=O)R, wherein R is alkyl, alkenyl, alkynyl, aryl, heteroaryl, substituted alkyl, substituted alkenyl, substituted alkynyl, substituted aryl or substituted heteroaryl.

The term "sulfate" as used herein is defined as —$SO_3H$ or —$SO_3M$, wherein M is a metal such as the nonlimiting examples of sodium, postassium, and lithium.

The term "carboxylate" as used herein is defined as —$CO_2H$ or —$CO_2M$, wherein M is a metal such as the nonlimiting examples of sodium, postassium, and lithium.

The term "haloalkyl" as used herein is defined as an alkyl group that is substituted with one or more halogens. Nonlimiting examples of haloalkyl groups include trifluoromethyl, difluoromethyl, chloromethyl, and the like.

The term "cyano" as used herein refers to a —C≡N group, also designated —CN.

The term "thioether" as used here is defined as —SR, wherein R is alkyl, alkenyl, alkynyl, aryl, heteroaryl, substituted alkyl, substituted alkenyl, substituted alkynyl, substituted aryl or substituted heteroaryl.

The term "electron donating group" as used herein refers to a substituent of an aryl or a heteroaryl group (inclusive of substituted aryl and heteroaryl groups) that tends to increases the electron density of the aryl or heteroaryl group. The ability of a substituent to act as an electron donating group is determined by the group's ability to donate electron density to an aromatic system (e.g., benzene) as compared to the ability of hydrogen to donate electron density to the system. Those substituents that are better at donating electron density to a given aromatic system than hydrogen are considered "electron donating groups." Nonlimiting examples of electron donating groups include alkyl, aryl, heteroaryl, alkenyl, hydroxyl, alkoxy, amido, and oxycarbonyl.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. Further, when an additive or UV absorbent is described as includable in an amount of a particular percentage "or less," e.g., "5% or less," the additive or UV absorbent can be included in an amount of at least 0.01% up to the percentage indicated.

Figure 2:
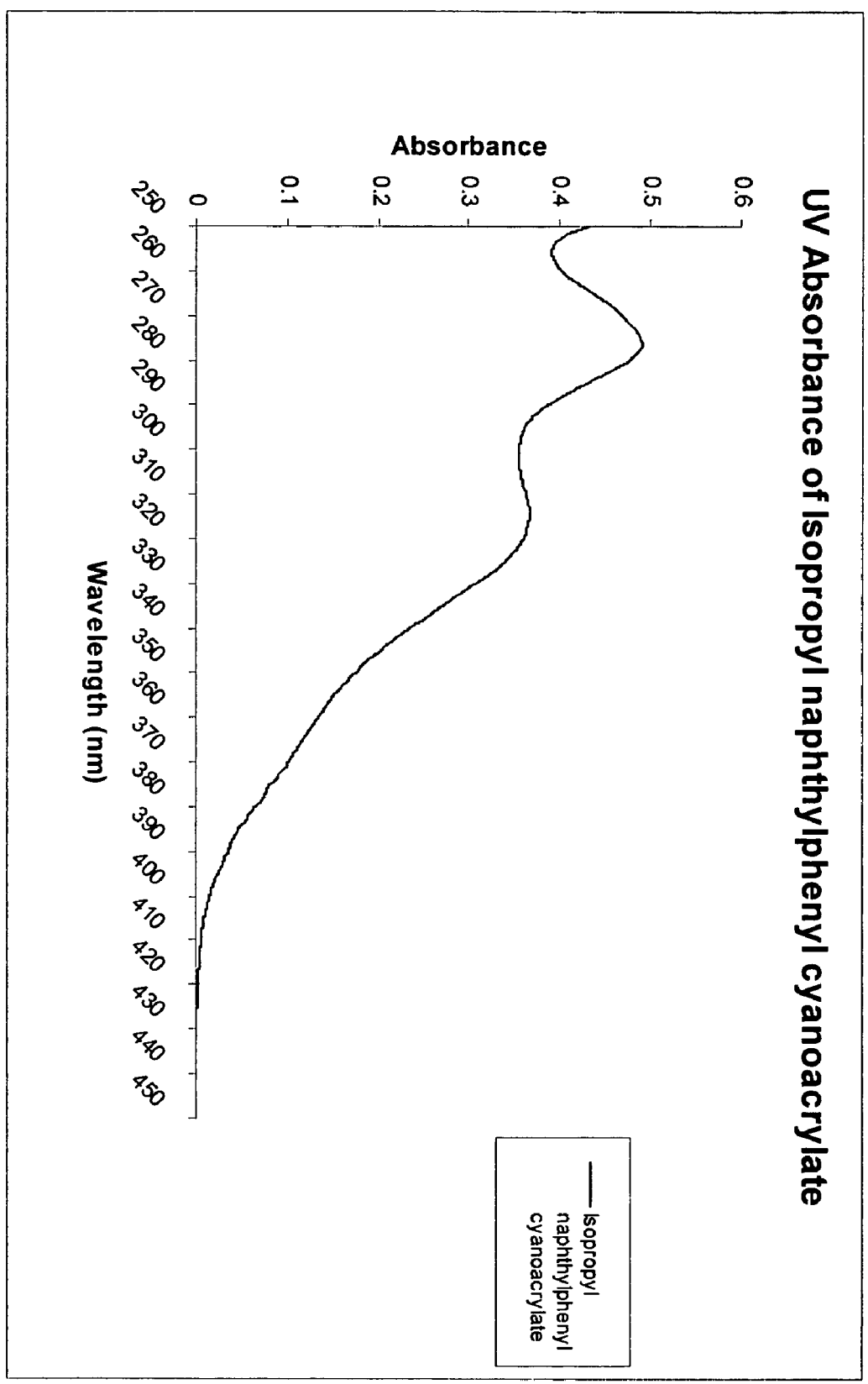
FIG. 2 is a graph of the UV absorbance of isopropyl naphthylphenyl cyanoacrylate of UV light having wavelength of 250 nm to 450 nm.

It has been found, quite surprisingly, that α-cyano-β-naphthyl acrylates are capable of absorbing light in the ultraviolet spectrum. It has also been found that α-cyano-β-naphthyl acrylates can be utilized as UV filters in a composition designed to protect a surface from UV degradation. FIGS. 1 and 2 show the UV absorbance of isopropyl naphthylmethyl cyanoacrylate and isopropyl naphthylphenyl cyanoacrylate, respectively, when contacted with UV light having wavelengths between 250 nm and 450 nm. The absorbance spectra of FIGS. 1 and 2 indicate that the α-cyano-β-naphthyl acrylate compounds absorb UV light across a wide range of wavelengths, and therefore can be useful as both UV-A and UV-B filters.

One embodiment of the compounds, compositions and methods described herein is a compound of formula (I):

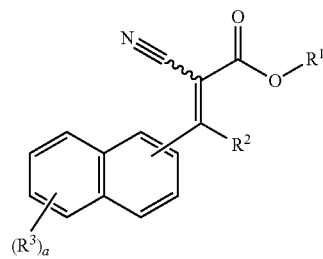

wherein $R^1$ is selected from the group consisting of $C_3$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; $R^2$ is selected from the group consisting of $C_2$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; $R^3$ is selected from the group consisting of hydroxyl, alkyl, alkenyl, alkynyl, alkoxy, halo, nitro, nitroso, alkylcarbonyl, alkoxycarbonyl, amino, substituted amino, amido, substituted amido, sulfate, carboxylate, oxycarbonyl, cycloalkyl, haloalkyl, cyano, and thioether, and a is in the range of 0 to 7. Preferably, $R^2$ is selected from the group consisting of aryl, substituted aryl, heteroaryl, and substituted heteroaryl, more preferably naphthyl, phenyl, substituted naphthyl, and substituted phenyl, and still more preferably $R^2$ is a naphthyl or a substituted naphthyl and the naphthyl or substituted naphthyl are attached to the compound of formula (I) at the 1-position or the 2-position of the naphthyl or substituted naphthyl. $R^2$ is also preferably selected from the group consisting of alkyl or substituted alkyl. Preferably, $R^1$ is selected from the group consisting of $C_3$-$C_{50}$ alkyl and $C_3$-$C_{50}$ substituted alkyl, more preferably isopropyl, n-propyl, n-butyl, sec-butyl, iso-butyl, tert-butyl, hexyl, and 2-ethylhexyl.

The preparation of α-cyano-β-naphthyl acrylates can be performed according to the following general scheme:

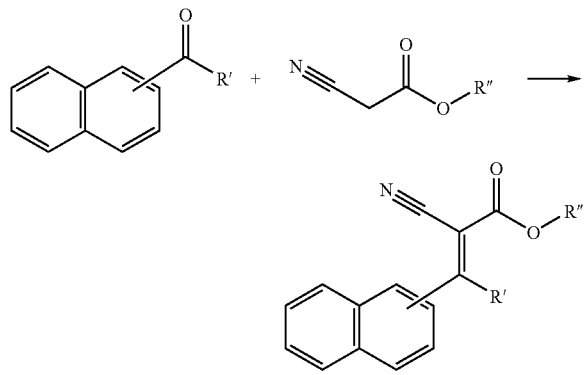

wherein, in a condensation reaction, a naphthyl ketone is reacted with a cyanopropionate to form the desired naphthyl cyanoacrylate (α-cyano-β-naphthyl acrylate) compound. Varying the identity of the starting ketone and cyanopropionate will produce to a wide range of UV absorbing acrylates.

It has been found, quite surprisingly, that the addition of substituents that increase the electron density of the π system of the aromatic rings tends to improve the electronic characteristics of the compounds such that the UV absorption and stabilization of the compounds is superior as compared to the compounds without electron donating substituents on the aromatic rings. Thus, preferred substituents on the aromatic ring(s) of a compound of formula (I) described herein are electron donating groups, more preferably the electron donating substituent(s) are selected from the group consisting of alkyl, alkenyl, aryl, alkoxy, amino, alkylamino, thioether, hydroxyl, oxycarbonyl and amido.

Compounds of formula (I), quite surprisingly, are able to absorb UV radiation and to increase the photostability of a photoactive compound in a sunscreen composition. The compounds are, therefore, able to be used to protect a surface (e.g., human skin) from the harmful effects of UV-radiation. FIG. 1 shows the absorbance spectra from 280 nm to 400 nm for isopropyl naphthylmethyl cyanoacrylate (a compound of formula (I) wherein $R^1$ is an iso-propyl group and $R^2$ is a methyl group and there is no substitution of the naphthyl ring). FIG. 2 is a graph of the absorbance spectra from 280 nm to 400 nm for isopropyl naphthylphenyl cyanoacrylate (a compound of formula (I) wherein $R^1$ is an iso-propyl group and $R^2$ is a methyl group and there is no substitution of the naphthyl and phenyl rings). FIGS. 1 and 2 confirms that compounds of formula (I) absorb UV-radiation in both the UV-A and UV-B ranges.

Accordingly, another embodiment of the compounds, compositions and methods described herein is a sunscreen composition comprising a compound of formula (I):

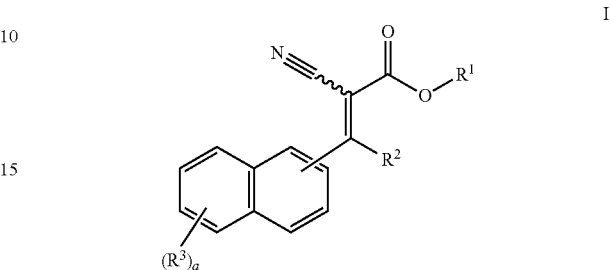

wherein $R^1$ and $R^2$ are the same or different and are selected from the group consisting of $C_1$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; $R^3$ is selected from the group consisting of hydroxyl, alkyl, alkenyl, alkoxy, halo, nitro, nitroso, alkylcarbonyl, alkoxycarbonyl, amino, substituted amino, amido, substituted amido, sulfate, carboxylate, oxycarbonyl, cycloalkyl, haloalkyl, cyano, and thioether, and a is in the range of 0 to 7. Preferably, $R^2$ is selected from the group consisting of aryl, substituted aryl, heteroaryl, and substituted heteroaryl, more preferably naphthyl, phenyl, substituted naphthyl, and substituted phenyl, and still more preferably $R^2$ is a naphthyl or a substituted naphthyl and the naphthyl or substituted naphthyl are attached to the compound of formula (I) at the 1-position or the 2-position of the naphthyl or substituted naphthyl. $R^2$ is also preferably selected from the group consisting of alkyl or substituted alkyl. Preferably, $R^1$ is selected from the group consisting of $C_3$-$C_{50}$ alkyl and $C_3$-$C_{50}$ substituted alkyl, more preferably isopropyl, n-propyl, n-butyl, sec-butyl, iso-butyl, tert-butyl, hexyl, and 2-ethylhexyl.

Commonly-assigned U.S. Pat. Nos. 6,485,713 and 6,537,529, the disclosures of which are hereby incorporated herein by reference, describe compositions and methods for increasing the photostability of photoactive compounds in a sunscreen composition, e.g., by the addition of polar solvents to the oil phase of a composition. It has been found, quite surprisingly, that by increasing the polarity of the oil phase of a sunscreen composition including a compound of formula (I), the stability of the sunscreen composition is increased. Thus, in a sunscreen described herein, preferably, one or more highly polar solvents are present in the oil-phase of the composition. Preferably, a sufficient amount of a polar solvent is present in a sunscreen composition to raise the dielectric constant of the oil-phase of the composition to a dielectric constant of at least about 7, preferably at least about 8.

The sunscreen compositions described herein contain a derivative of an α-cyano-β-naphthyl acrylate compound in the range of about 0.1% by weight based on the total weight of the composition to about 50% by weight. Preferably, the α-cyano-β-naphthyl acrylate compound is present in the range of about 0.5% to about 15% by weight, and still more preferably in the range of about 1% to about 8% by weight.

A sunscreen composition can be combined into a cosmetically acceptable carrier, optionally including emollients, stabilizers, and emulsifiers, such as those known in the art, and combinations thereof. These additives can be used in preparing an aqueous emulsion portion or phase of the sunscreen composition for admixture with an oil portion or phase that includes one or more photoactive compounds and one or more organic solvents for the photoactive compounds. When made, preferably the emulsion is an oil-in-water emulsion.

The sunscreen composition described herein can be combined with cosmetically acceptable sunscreen additives, including emollients, stabilizers, emulsifiers, thickeners, humectants, surfactants, preservatives, vitamins, antifoaming agents, fragrances, anti-irritants, silicones and organomodified silicones, chelators, opacifiers, polar oils, nonpolar oils, waxes, alcohols, polyols, propellants, colorants, pigments, and combinations thereof. These additives can be used in preparing an emulsion from an aqueous system and a mixture of a filter system that includes one or more photoactive compounds and a solvent system that includes one or more organic solvents. The term "cosmetically acceptable carrier" as used herein, means that the carrier and its components are suitable for use in contact with human skin without undue toxicity, incompatibility, instability, allergic response, and the like. Such carriers are well-known to one of ordinary skill in the art, and can include one or more compatible liquid or solid filler diluents or vehicles which are suitable for administration to human skin.

UV-A radiation (about 320 nm to about 400 nm), is recognized as contributing to causing damage to skin. The sunscreen compositions described herein preferably include a UV-A photoactive compound such as a dibenzoylmethane derivative UV-A photoactive compound in an amount of about 0.1% by weight to about 10% by weight. Preferred dibenzoylmethane derivatives include, 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

The sunscreen compositions described herein can include a variety of photoactive compounds, and preferably include at least one UV-A photoactive compound and at least one UV-B photoactive compound. The sunscreen compositions described herein may include one or more photoactive compounds, each in an amount of about 0.1% by weight to about 10% by weight, selected from the group consisting of p-aminobenzoic acid and salts and derivatives thereof; anthranilate and derivatives thereof; dibenzoylmethane and derivatives thereof; salicylate and derivatives thereof; cinnamic acid and derivatives thereof; dihydroxycinnamic acid and derivatives thereof; camphor and salts and derivatives thereof; trihydroxycinnamic acid and derivatives thereof; dibenzalacetone naphtholsulfonate and salts and derivatives thereof; benzalacetophenone naphtholsulfonate and salts and derivatives thereof; dihydroxy-naphthoic acid and salts thereof; o-hydroxydiphenyldisulfonate and salts and derivatives thereof; p-hydroxydiphenyldisulfonate and salts and derivatives thereof; coumarin and derivatives thereof; diazole derivatives; quinine derivatives and salts thereof; quinoline derivatives; hydroxy-substituted benzophenone derivatives; methoxy-substituted benzophenone derivatives; uric acid derivatives; vilouric acid derivatives; tannic acid and derivatives thereof; hydroquinone; benzophenone derivatives; 1,3,5-triazine derivatives, phenyldibenzimidazole tetrasulfonate and salts and derivatives thereof; terephthalylidene dicamphor sulfonic acid and salts and derivatives thereof; methylene bis-benzotriazolyl tetramethylbutylphenol and salts and derivatives thereof; bis-ethylhexyloxyphenol methoxyphenyl triazine and salts and derivatives thereof; diethylamino hydroxybenzoyl hexyl benzoate and salts and derivatives thereof; and combinations of the foregoing.

In addition, UV filters from the following categories (with specific examples) are also useful in the sunscreen compositions described herein, each in an amount of about 0.1% by weight to about 10% by weight: p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3-benzylidene, 4-methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone; benzalacetophenone; naphtholsulfonates (sodium salts of 2-naphthol-3,6-disulfonic and of 2-naphthol-6,8-disulfonic acids); dihydroxy-naphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric acid derivatives; vilouric acid derivatives; tannic acid and its derivatives; hydroquinone; and benzophenones (oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone, 4-isopropyldibenzoylmethane, butylmethoxydibenzoylmethane, etocrylene, and 4-isopropyl-dibenzoylmethane).

Particularly useful UV filters for use in the sunscreen compositions described herein, present individually in an amount of about 0.1% by weight to about 10% by weight, include: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexyl-2-cyano-3,3-diphenylacrylate, 2-ethylhexylsalicylate, glycerol p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl-5-sulfoniobenzoxazoic acid, and combinations of the foregoing.

A preferred combination of photoactive compounds in the sunscreen compositions described herein include a UV-A photoactive compound, such as a dibenzoylmethane derivative, and a UV-B photoactive compound. However, when 2-ethylhexyl-p-methoxycinnamate is included in the sunscreen composition together with a dibenzoylmethane derivative, the dibenzoylmethane derivative can become particularly unstable. Without intending to be limited to any particular mechanism, it is believed that the cinnamate ester reacts with an excited-state dibenzoylmethane derivative in a bimolecular pathway that renders both the dibenzoylmethane derivative and the cinnamate ester incapable of absorbing UV radiation. It has been found, quite surprisingly, that the α-cyano-β-naphthyl acrylate derivatives described herein unexpectedly increase the stability of a sunscreen composition that includes both 2-ethylhexyl-p-methoxycinnamate and a dibenzoylmethane derivative. Thus, one embodiment of the sunscreen compositions described herein includes 2-ethylhexyl-p-methoxycinnamate, a dibenzoylmethane derivative, and a α-cyano-β-naphthyl acrylate derivative.

For a product marketed in the United States, cosmetically-acceptable photoactive compounds and concentrations (reported as a percentage by weight of the total cosmetic sunscreen composition) useful in the sunscreen compositions described herein, in the indicated percentages, include one or more of the following photoactive compounds: aminobenzoic acid (also called para-aminobenzoic acid and PABA) 15% or less; avobenzone (also called butyl methoxy dibenzoylmethane) 3% or less; cinoxate (also called 2-ethoxyethyl p-methoxycinnamate) 3% or less; dioxybenzone (also called benzophenone-8) 3% or less; homosalate, 15% or less; menthyl anthranilate (also called menthyl 2-aminobenzoate) 5% or less; octocrylene (also called 2-ethylhexyl-2-cyano-3,3 diphenylacrylate) 10% or less; octinoxate (also called octyl methoxycinnamate and 2-ethylhexyl methoxycinnamate), 7.5% or less; octisalate (also called octyl salicylate and 2-ethylhexyl salicylate) 5% or less; oxybenzone (also called benzophenone-3) 6% or less; padimate O (also called octyl dimethyl PABA) 8% or less; phenylbenzimidazole sulfonic acid (also called eunsulizole), 4% or less; sulisobenzone (also called benzophenone-4) 10% or less; and trolamine salicylate (also called triethanolamine salicylate) 12% or less; zinc oxide, 25% or less; and titanium oxide, 25% or less.

Other cosmetically-acceptable photoactive compounds and preferred concentrations (percent by weight of the total cosmetic sunscreen composition) useful in the sunscreen compositions described herein, in the indicated percentages include diethanolamine methoxycinnamate, 10% or less; ethyl-[bis(hydroxypropyl)]aminobenzoate, 5% or less; glyceryl aminobenzoate, 3% or less; 4-isopropyl dibenzoylmethane, 5% or less; 4-methylbenzylidene camphor, 6% or less; terephthalylidene dicamphor sulfonic acid, 10% or less; and sulisobenzone (also called benzophenone-4) 10% or less.

For a product marketed in the European Union, cosmetically-acceptable photoactive compounds and concentrations (reported as a percentage by weight of the total cosmetic sunscreen composition) useful in the sunscreen compositions described herein, in the indicated percentages include: PABA, 5% or less; camphor benzalkonium methosulfate, 6% or less; homosalate, 10% or less; benzophenone-3, 10% or less; phenylbenzimidazole sulfonic acid or acid derivative, 8% or less, calculated as weight of acid; terephthalidene dicamphor sulfonic acid or acid derivative, 10% or less, calculated as weight of acid; butyl methoxydibenzoylmethane, 5% or less; benzylidene camphor sulfonic acid or acid derivative, 6% or less, calculated as weight of acid; octocrylene or octocrylene derivative, 10% or less, calculated as weight of acid; polyacrylamidomethyl benzylidene camphor, 6% or less; ethylhexyl methoxycinnamate, 10% or less; PEG-25 PABA, 10% or less; isoamyl p-methoxycinnamate, 10% or less; ethylhexyl triazone, 5% or less; drometrizole trilloxane, 15% or less; diethylhexyl butamido triazone, 10% or less; 4-methylbenzylidene camphor, 4% or less; 3-benzylidene camphor, 2% or less; ethylhexyl salicylate, 5% or less; ethylhexyl dimethyl PABA, 8% or less; benzophenone-4 or benzophenone derivative, 5%, calculated as weight of acid; methylene bis-benztriazolyl tetramethylbutylphenol, 10% or less; disodium phenyl dibenzimidazole tetrasulfonate or phenyl dibenzimidazole derivative, 10% or less, calculated as weight of acid; bis-ethylhexyloxyphenol methoxyphenol triazine, 10% or less; methylene bisbenzotriazolyl tetramethylbutylphenol (also called TINOSORB M) 10% or less; bisethylhexyloxyphenol methoxyphenyl triazine (also called TINOSORB S) 10% or less; and diethylamino hydroxybenzoyl hexyl benzoate (also known as UVINUL A PLUS) 10% or less.

All of the above-described UV filters are commercially available and useful in the compositions described herein, together with one or more derivatives of α-cyano-β-naphthyl acrylate as a single photoactive addition or in any combination. For example, suitable commercially-available organic UV filters useful in the compositions described herein are identified by trade name and supplier in Table I.

TABLE I

| CTFA Name | Trade Name | Supplier |
|---|---|---|
| benzophenone-3 | UVINUL M-40 | BASF Chemical Co. |
| benzophenone-4 | UVINUL MS-40 | BASF Chemical Co. |
| benzophenone-8 | SPECTRA-SORB UV-24 | American Cyanamid |
| DEA-methoxycinnamate | BERNEL HYDRO | Bernel Chemical |
| ethyl dihydroxypropyl-PABA | AMERSCREEN P | Amerchol Corp. |
| glyceryl PABA | NIPA G.M.P.A. | Nipa Labs. |
| homosalate | KEMESTER HMS | Humko Chemical |
| menthyl anthranilate | SUNAROME UVA | Felton Worldwide |
| octocrylene | UVINUL N-539 | BASF Chemical Co. |
| octyl dimethyl PABA | AMERSCOL | Amerchol Corp. |
| octyl methoxycinnamate | PARSOL MCX | Bernel Chemical |
| PABA | PABA | National Starch |
| 2-phenylbenzimidazole-5-sulphonic acid | EUSOLEX 6300 | EM Industries |
| TEA salicylate | SUNAROME W | Felton Worldwide |
| 2-(4-methylbenzildene)-camphor | EUSOLEX 6300 | EM Industries |
| benzophenone-1 | UVINUL 400 | BASF Chemical Co. |
| benzophenone-2 | UVINUL D-50 | BASF Chemical Co. |
| benzophenone-6 | UVINUL D-49 | BASF Chemical Co. |
| benzophenone-12 | UVINUL 408 | BASF Chemical Co. |
| 4-isopropyl dibenzoyl methane | EUSOLEX 8020 | EM Industries |
| butyl methoxy dibenzoyl methane | PARSOL 1789 | Givaudan Corp. |
| etocrylene | UVINUL N-35 | BASF Chemical Co. |
| methylene bisbenzotriazolyl tetramethylbutylphenol | TINOSORB M | Ciba Specialty Chemicals |
| bisethylhexyloxyphenol methoxyphenyl triazine. | TINOSORB S | Ciba Specialty Chemicals |
| diethylamino hydroxybenzoyl hexyl benzoate | UVINUL A PLUS | BASF Chemical Co. |

Metal oxides have also been found to be useful in sunscreen compositions based upon their ability to increase the photoprotective properties of the composition. Microfine metal oxides are of particular interest in sunscreen applications. In one embodiment, the compositions described herein include a metal oxide, in an amount of about 0.1% by weight to about 25% by weight, and a α-cyano-β-naphthyl acrylate derivative, more specifically, a microfine metal oxide and a α-cyano-β-naphthyl acrylate derivative. The average particle diameter of the microfine metal oxide preferably is less than 100 μm, e.g., from 0.1 μm to 100 μm, particularly advantageously less than 50 μm, e.g., from 0.1 μm to 50 μm. In the sunscreen compositions described herein, the metal oxide can be in any shape or form (platelets, rods, spheres, or the like). Nonlimiting examples of preferred metal oxides include uncoated titanium dioxide, coated titanium dioxide, uncoated zinc oxide, and coated zinc oxide, useful alone or in any combination.

Due to the lipophilic character of the α-cyano-β-naphthyl acrylate derivatives described herein and dibenzoylmethane derivatives, the sunscreen compositions described herein preferably contain at least one fatty phase. The fatty phase can take the form of oily or oleoalcoholic lotions or of fatty or oleoalcoholic gels, solid sticks, emulsions such as a cream or milk or of vesicular dispersions of ionic or nonionic amphiphilic lipids. In one embodiment, the sunscreen compositions described herein can be in the form of an aerosol spray.

A solubilization solvent can be used to dissolve the α-cyano-β-naphthyl acrylate derivatives described herein in the oily phase of the sunscreen compositions described herein. Preferably, the solubilization solvent is an oil, wax, lower polyol, polyol ester of fatty acids, alkyl ester of a fatty acid or diacid, monohydric alcohol, fatty alcohol, liquid paraffin, fatty ether, squalane, ester oil, amide or mixtures thereof. Preferred solubilization solvents include capric triglycerides (polyol esters of fatty acids), $C_{12-15}$ alkyl benzoates and phenylethyl benzoate (aromatic esters), diisopropyl adipate, dioctyl maleate, diethylhexyl sebacate, octyl palmitate, isopropyl myristate and isopropyl palmitate (alkyl esters of fatty acids and diacids), dicapryl ether and PEG-8 (fatty ethers), isooctane, isododecane and isohexadecane (liquid paraffins), dimethyl capramide (amides), cetyl alcohol, stearyl alcohol and behenyl alcohol (fatty alcohols), dimethicones and polysiloxanes (silicone oils), carnauba wax and paraffin waxes (wax), diglycerides and triglycerides (esters of fatty acids), perfluoropolyethers, VASELINE and lanolin (oils), ceresin, and mixtures thereof.

When the compositions described herein are produced in the form of an emulsion, the aqueous phase can contain one or more water-soluble UV absorbing compound such as benzene-1,4-bis(3-methylidene-10-camphorsulfonic acid), 2-phenylbenzimidazole-5-sulphonic acid or 2-hydroxy-4-methoxybenzophenone-5-sulfonic acid (UVINUL MS 40). These acids can optionally be in a salt form, e.g., metal salts.

Topical carriers used in the sunscreen compositions described herein can be in a wide variety of forms. For example, emulsion carriers, including, but not limited to, oil-in-water, water-in-oil, water-in-oil-in-water, and oil-in-(water or polyol)-in-silicone emulsions, water-in-silicone, and polyol-in-silicone emulsions are useful herein. These emulsions can cover a broad range of viscosities (e.g., from about 100 cps to about 500,000 cps). These emulsions can also be delivered in the form of sprays using either mechanical pump containers or pressurized aerosol containers using conventional propellants. These carriers can also be delivered in the form of a mousse. Other suitable topical carriers include aqueous-based single phase solvents (e.g., water, alcohols, glycols, polyols, and the like).

When the sunscreen compositions described herein are in the form of an aerosol spray or mousse, the carrier can also utilize any of the conventional propellants to deliver the material as a foam (in the case of a mousse) or as a fine, uniform spray (in the case of an aerosol). Examples of suitable propellants include materials such as trichlorofluoromethane, dichlorodifluoromethane, difluoroethane, dimethylether, propane, n-butane or isobutane. Suitable spray containers are well known in the art and include conventional, non-aerosol pump sprays (i.e., "atomizers"), aerosol containers, cans containg a propellant (e.g., compressed air).

It has also been found that α-cyano-β-naphthyl acrylates are able to quench (accept the excited state energy), and thereby, photostabilize an excited photoactive compound. Without intending to be limited to any particular mechanism by which an α-cyano-β-naphthyl acrylate is capable of quenching the excited state of a photoactive compound, it is theorized that the α-cyano-β-naphthyl acrylate accepts the excited state energy and dissipates the energy kinetically in the form of rapid isomerizations of the acrylate double bond. This theoretical mechanism is depicted below:

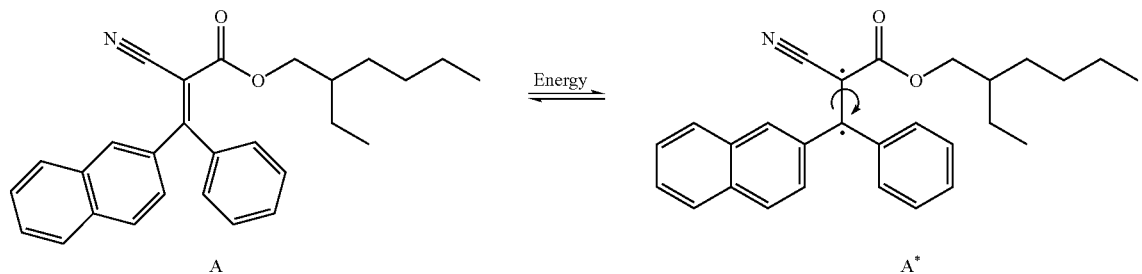

A

A* wherein (2E)-5-ethyl-2-[2-naphthyl(phenyl)methylene]-3-oxononanenitrile (shown above as structure A) accepts triplet excited state energy and forms a diradical (shown above as structure A*) at the α and β positions of the acrylate, which converts the double bond into a single bond and allows for free rotation about the single bond. This rotation occurs rapidly and efficiently to dissipate excited state energy accepted by a derivative of α-cyano-β-naphthyl acrylate. It is the ability of the compound to accept the triplet excited state energy from a photoactive compound and form a diradical at the α and β positions of the acrylate, which converts the double bond to a single bond and allows for the free rotation about this newly formed single bond. This rotation occurs rapidly and efficiently to dissipate any excited energy accepted by the cyanoacrylate compound from the other photoactive compound. In solution (e.g., a sunscreen composition), a key limitation on the ability of a compound to photostabilize another compound is the ability of the two compounds to come into contact with each other.

Compounds of formula (I) are able to absorb UV radiation, and in a composition, the compounds of formula (I) can protect a surface (e.g., human skin) from the harmful effects of UV-radiation. Accordingly, another embodiment of the compounds, compositions and methods described herein is a method of protecting a surface from ultraviolet radiation including the step of topically applying to the surface, in an acceptable carrier, a composition comprising a compound of formula (I):

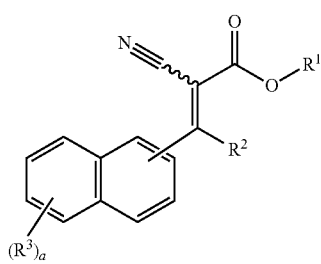

wherein $R^1$ and $R^2$ are the same or different and are selected from the group consisting of $C_1$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; $R^3$ is selected from the group consisting of hydroxyl, alkyl, alkenyl, alkoxy, halo, nitro, nitroso, alkylcarbonyl, alkoxycarbonyl, amino, substituted amino, amido, substituted amido, sulfate, carboxylate, oxycarbonyl, cycloalkyl, haloalkyl, cyano, and thioether, and a is in the range of 0 to 7. Preferably, the surface is human shin and the carrier is a cosmetically acceptable carrier. Preferably, $R^2$ is selected from the group consisting of aryl, substituted aryl, heteroaryl, and substituted heteroaryl, more preferably naphthyl, phenyl, substituted naphthyl, and substituted phenyl, and still more preferably $R^2$ is a naphthyl or a substituted naphthyl and the naphthyl or substituted naphthyl are attached to the compound of formula (I) at the 1-position or the 2-position of the naphthyl or substituted naphthyl. $R^2$ is also preferably selected from the group consisting of alkyl or substituted alkyl. Preferably, $R^1$ is selected from the group consisting of $C_3$-$C_{50}$ alkyl and $C_3$-$C_{50}$ substituted alkyl, more preferably isopropyl, n-propyl, n-butyl, sec-butyl, iso-butyl, tert-butyl, hexyl, and 2-ethylhexyl.

As shown in FIG. 2, the range within which compounds of formula (I) absorb UV radiation suggest that compounds of formula (I) can be used as UV-B filters in a sunscreen composition. It is well known that oxybenzone (also referred to as benzophenone-3) is commonly used as a UV-B filter in commercially available sunscreen composition, however, oxybenzone also is beginning to be recognized as a potential harmful effects of oxybenzone to human skin. Accordingly, it is contemplated that compounds of formula (I) can be used as a substitute for oxybenzone in a sunscreen composition designed to achieve photoprotection over the UV-B range. Preferably, the substitute for oxybenzone is a compound of formula (I) wherein $R^1$ is an alkyl group and $R^2$ is an aryl group, more preferably, $R^1$ is a $C_2$-$C_{10}$ alkyl group and $R^2$ is a phenyl group. As shown in FIG. 2, isopropyl naphthylphenyl cyanoacrylate (a compound of formula (I) wherein $R^1$ is an iso-propyl group and $R^2$ is a methyl group and there is no substitution of the naphthyl and phenyl rings) absorbs UV radiation over the UV-B range, with an absorbance comparable to oxybenzone.

The absorption process causes a photoactive compound to reach an excited state, wherein the excited state is characterized by the presence of excited energy (e.g., singlet energy or triplet energy), as compared to the ground state of the photoactive compound. Once a photoactive compound reaches an excited state there exists a number of pathways by which the excited photoactive compound can dissipate its excess energy (e.g., triplet energy), however, many of those pathways adversely affect the ability of the photoactive compound to further absorb UV radiation. The problem with dibenzoylmethane derivatives is that once they reach an excited state, they often become unstable. Upon radiation with UV light, the dibenzoylmethane derivative can rapidly decompose and thereby lose its UV-A absorbing effect. The addition of a photoactive compound, such as a highly-conjugated cyanoacrylate derivative of formula (I) to a composition that contains a dibenzoylmethane derivative can be used as a means to stabilize the photo-unstable dibenzoylmethane derivative, allowing it to maintain its UV-A filter properties for a longer period of time. Without intending to be limited to any particular mechanism of achieving this increase in stability, it is believed that the cyanoacrylate derivative stabilizes a dibenzoylmethane derivative by accepting the triplet energy of the dibenzoylmethane derivative once the dibenzoylmethane derivative has reached an excited state as a result of the absorption of ultra-violet light. Once a dibenzoylmethane derivative is excited, it is prone to degrade according to a number of pathways; however, the degradation of the dibenzoylmethane derivative can be substantially reduced or prevented by the use of a highly-conjugated cyanoacrylate derivative to quench (accept) the triplet excited state energy present in an excited dibenzoylmethane molecule.

Thus, in one pathway of degradation, a dibenzoylmethane derivative is excited to its triplet state and the excited state triplet energy is released in a bond breaking step, thereby preventing the dibenzoylmethane derivative from further accepting ultra-violet radiation. A highly-conjugated cyanoacrylate derivative by accepting the triplet state (excited state) energy of the excited dibenzoylmethane derivative in such a way as to convert the excited dibenzoylmethane derivative back to a ground state that is capable of reaccepting ultra-violet radiation (energy transfer). Thus, another embodiment of the compounds, composition, and methods described herein is a method of photostabilizing a dibenzoylmethane derivative with the addition of an amount of a compound of formula (I):

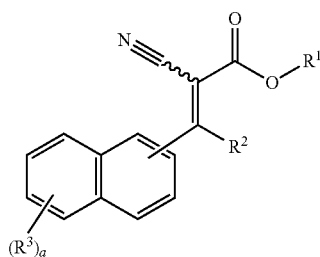

wherein $R^1$ is selected from the group consisting of $C_1$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; $R^2$ is selected from the group consisting of $C_2$-$C_{50}$ alkyl, $C_2$-$C_{50}$ alkenyl, $C_2$-$C_{50}$ alkynyl, $C_3$-$C_8$ cycloalkyl, $C_2$-$C_7$ heterocycloalkyl, aryl, $C_1$-$C_{50}$ polyether, $C_1$-$C_{50}$ substituted alkyl, $C_3$-$C_8$ substituted cycloalkyl, $C_2$-$C_{50}$ substituted alkenyl, $C_2$-$C_{50}$ substituted alkynyl, $C_2$-$C_7$ substituted heterocycloalkyl, substituted aryl, heteroaryl, and substituted heteroaryl; $R^3$ is selected from the group consisting of hydroxyl, alkyl, alkenyl, alkynyl, alkoxy, halo, nitro, nitroso, alkylcarbonyl, alkoxycarbonyl, amino, substituted amino, amido, substituted amido, sulfate, carboxylate, oxycarbonyl, cycloalkyl, haloalkyl, cyano, and thioether, and a is in the range of 0 to 7. Preferably, $R^2$ is selected from the group consisting of aryl, substituted aryl, heteroaryl, and substituted heteroaryl, more preferably naphthyl, phenyl, substituted naphthyl, and substituted phenyl, and still more preferably $R^2$ is a naphthyl or a substituted naphthyl and the naphthyl or substituted naphthyl are attached to the compound of formula (I) at the 1-position or the 2-position of the naphthyl or substituted naphthyl. $R^2$ is also preferably selected from the group consisting of alkyl or substituted alkyl. Preferably, $R^1$ is selected from the group consisting of $C_3$-$C_{50}$ alkyl and $C_3$-$C_{50}$ substituted alkyl, more preferably isopropyl, n-propyl, n-butyl, sec-butyl, iso-butyl, tert-butyl, hexyl, and 2-ethylhexyl.

A photoactive compound can be considered stable when, for example, after 30 MED irradiation the photoactive compound has retained at least about 90% of its original absorbance at a wavelength, or over a range of wavelengths of interest (e.g., the wavelength at which a photoactive compound has a peak absorbance, such as 350-370 nm for avobenzone). Likewise, a sunscreen composition can include a plurality of photoactive compounds and a sunscreen composition, as a whole, can be considered stable when, for example, after 30 MED irradiation the sunscreen composition has retained at least about 90% of its original absorbance at one or more wavelengths of interest (e.g., at or near the peak absorbance wavelength of the primary photoactive compound).

EXAMPLES

The following examples are provided to illustrate the compounds, compositions, and methods described herein but are not intended to limit the scope of the compounds, compositions, and methods described herein.

Example 1

The method of preparing and using these highly conjugated cyanoacrylate derivatives is outlined below. A pictorial representation of the reaction to form isopropyl naphthylphenyl cyanoacrylate is shown below:

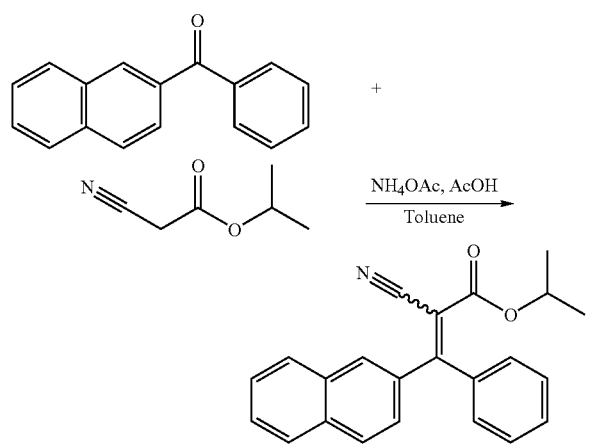

In a 500 mL 3-neck round bottom flask 24.34 g of 2-naphthyl phenyl ketone, 17.32 g of isopropyl cyanopropionate, 0.807 g of ammonium acetate, 40 mL of acetic acid, and 200 mL of toluene were added. The flask was then equipped with a mechanical stirrer, Dean-Stark apparatus, condenser and receiver, and the entire assembly was placed under an inert (nitrogen) atmosphere. The solution was refluxed for six hours, and an additional 0.807 g of ammonium acetate was added. The reaction was then refluxed for twelve hours. The reaction was then brought to room temperature and washed successively with 150 mL water, 150 mL dilute sodium bicarbonate, and another 150 mL water. The solution was then dried with anhydrous sodium sulfate, filtered, and the solvents removed. The crude product was recrystallized from a 1:3 mixture of ethyl acetate and hexanes, resulting in 24.7 g of the desired isopropyl naphthylphenyl cyanoacrylate as a mixture of the E and Z forms in greater than 99% purity.

Example 2

Sunscreen compositions were made by mixing the materials shown in Table II below:

TABLE II

| Ingredient | Cyanoacrylate Composition (% by weight) | Benzophenone-3 Composition (% by weight) | Octocrylene Composition (% by weight) |
|---|---|---|---|
| Oil Phase/UV Filters | | | |
| Isopropyl naphthylphenyl cyanoacrylate | 4.00 | 0 | 0 |
| Benzophenone-3 | 0 | 4.00 | 0 |
| Octocrylene | 0 | 0 | 4.00 |
| Avobenzone | 3.00 | 3.00 | 3.00 |
| Octisalate | 5.00 | 5.00 | 5.00 |
| Homosalate | 7.50 | 7.50 | 7.50 |
| Dimethyl capramide | 1.00 | 1.00 | 1.00 |
| Phenylethyl benzoate | 5.00 | 5.00 | 5.00 |
| Dimethicone | 0.40 | 0.40 | 0.40 |
| Benzyl alcohol | 0.50 | 0.50 | 0.50 |
| $C_{30}$–$C_{38}$ olefin/isopropyl maleate/methacrylate copolymer | 0.80 | 0.80 | 0.80 |
| Emulsifiers | | | |
| Stearic acid | 3.20 | 3.20 | 3.20 |
| Sorbitan isostearate | 4.00 | 4.00 | 4.00 |
| Polyglyceryl-3 distearate | 3.00 | 3.00 | 3.00 |
| Water Phase | | | |
| Disodium EDTA | 0.05 | 0.05 | 0.05 |
| Carbomer Ultrez 10 | 0.05 | 0.05 | 0.05 |
| Butylene glycol | 5.00 | 5.00 | 5.00 |
| Phenoxyethanol, Methyl paraben, Ethyl paraben, Propyl paraben, and Isobutyl paraben | 0.60 | 0.60 | 0.60 |
| Other Ingredients | | | |
| Triethanolamine | 2.03 | 2.03 | 2.03 |
| Water | 54.87 | 54.87 | 54.87 |
| Total | 100.00 | 100.00 | 100.00 |

The oil phase ingredients and the emulsifiers were blended together and heated to between 85° C. and 95° C. The disodium EDTA was dissolved in the water, then the carbomer ULTREZ 10 was added to form an aqueous solution. The resulting aqueous solution was then heated to between 85° C. and 95° C. Separately, the butylene glycol, phenoxyethanol, paraben preservatives, and triethanolamine were blended together and then added to the heated aqueous solution. The oil phase ingredients were then added, while maintaining the temperature of the resulting mixture between 85° C. and 95° C., and the resulting mixture was stirred for five minutes. The mixture wass then homogenized for three minutes. The mixture was then stirred while the mixture cooled to about 45° C. The amount of water was adjusted to account for water lost through evaporation in the above-described procedure. Stirring was continued until the mixture was uniform and homogenous.

Figure 3:
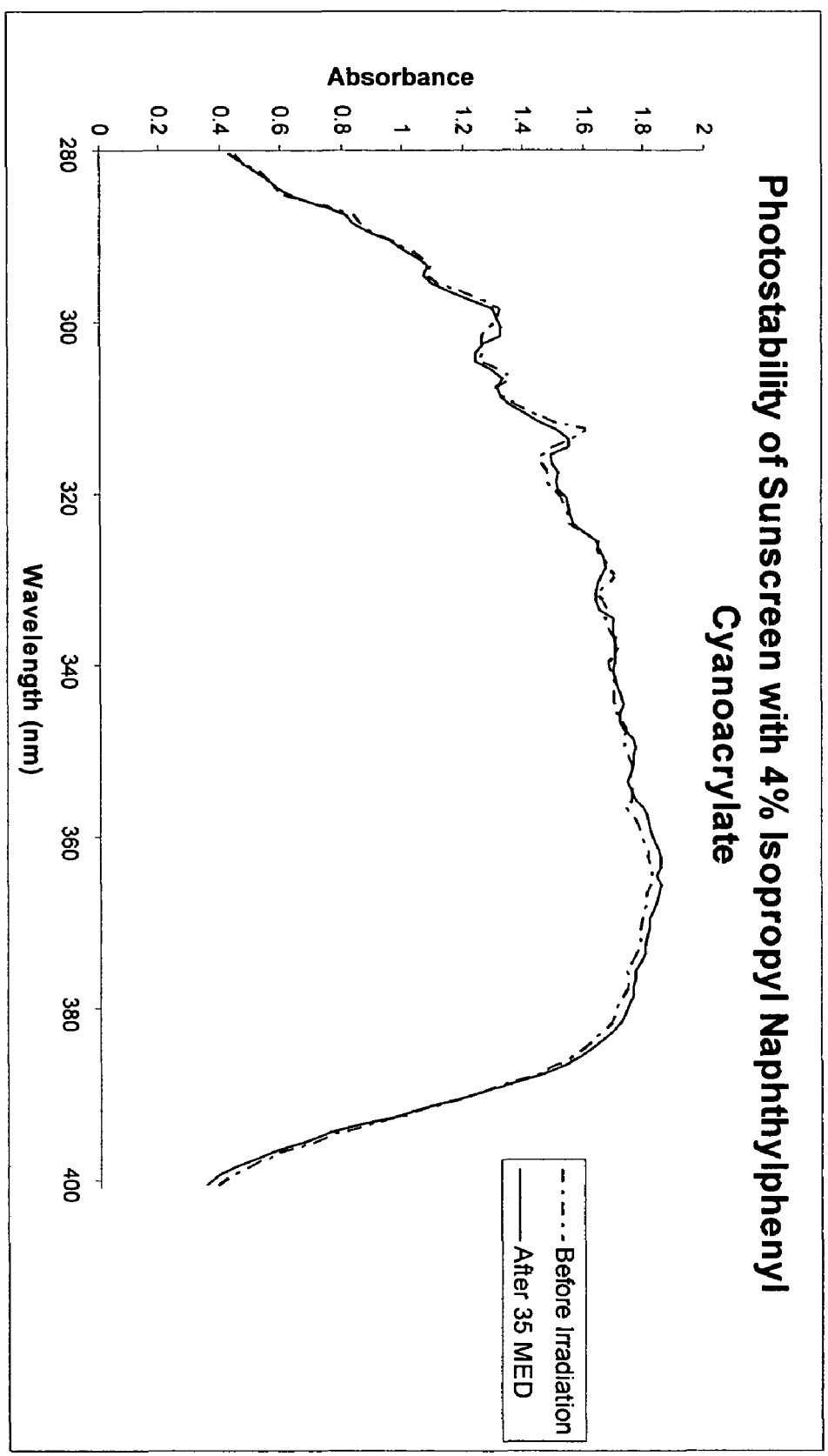
FIG. 3 is a graph of the absorbance of a sunscreen composition that includes 4% by weight isopropyl naphthylphenyl cyanoacrylate and 3% by weight avobenzone before and after irradiation of 35 MED, wherein, by definition, 1 MED is 21 millijoules per square centimeter (mJ/cm$^2$), of UV light having a wavelength of 280 nm to 400 nm.
Figure 4:
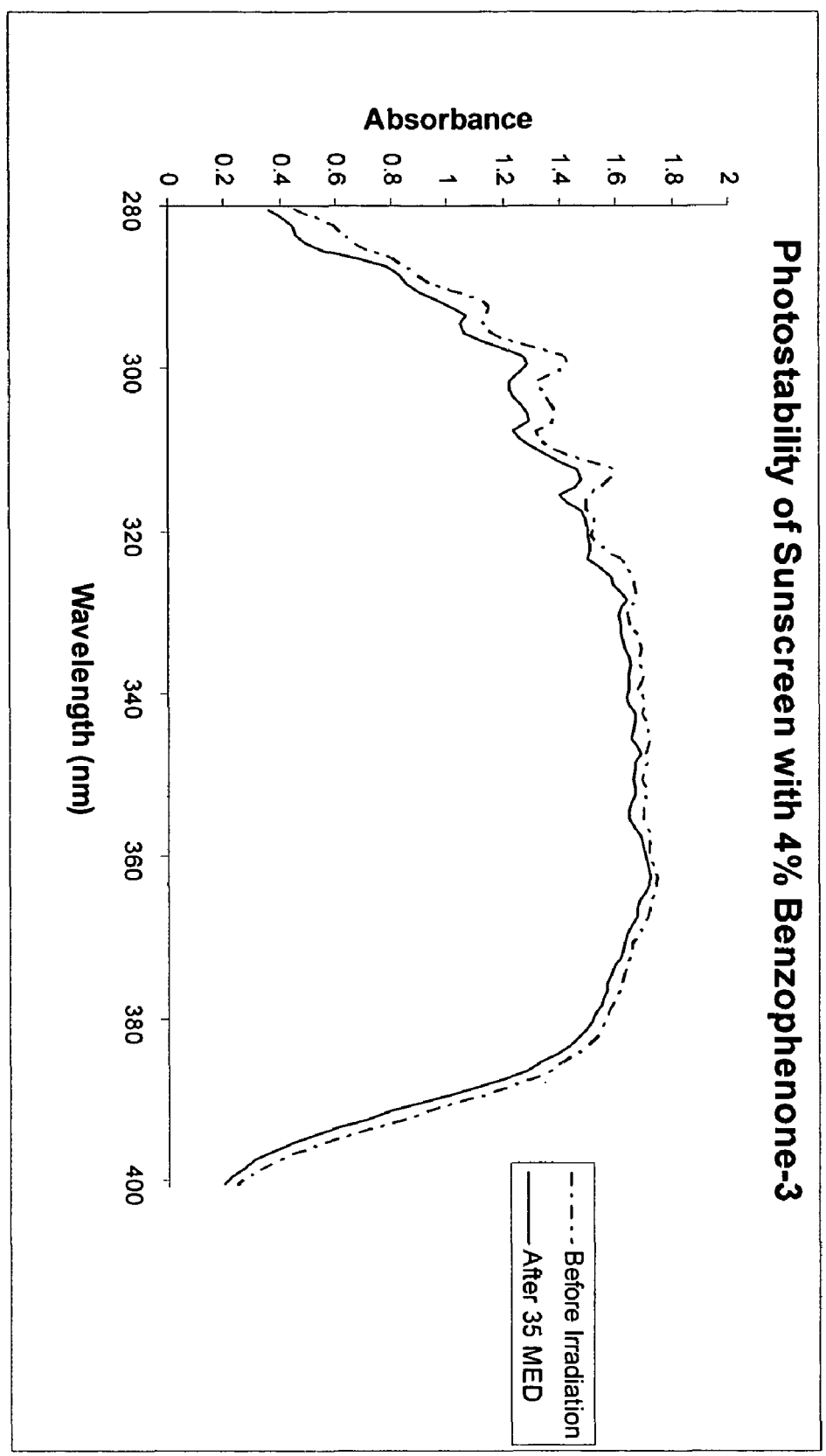
FIG. 4 is a graph of the absorbance of a sunscreen composition that includes 4% by weight benzophenone-3 and 3% by weight avobenzone before and after irradiation of 35 MED of UV light having a wavelength of 280 nm to 400 nm.
Figure 5:
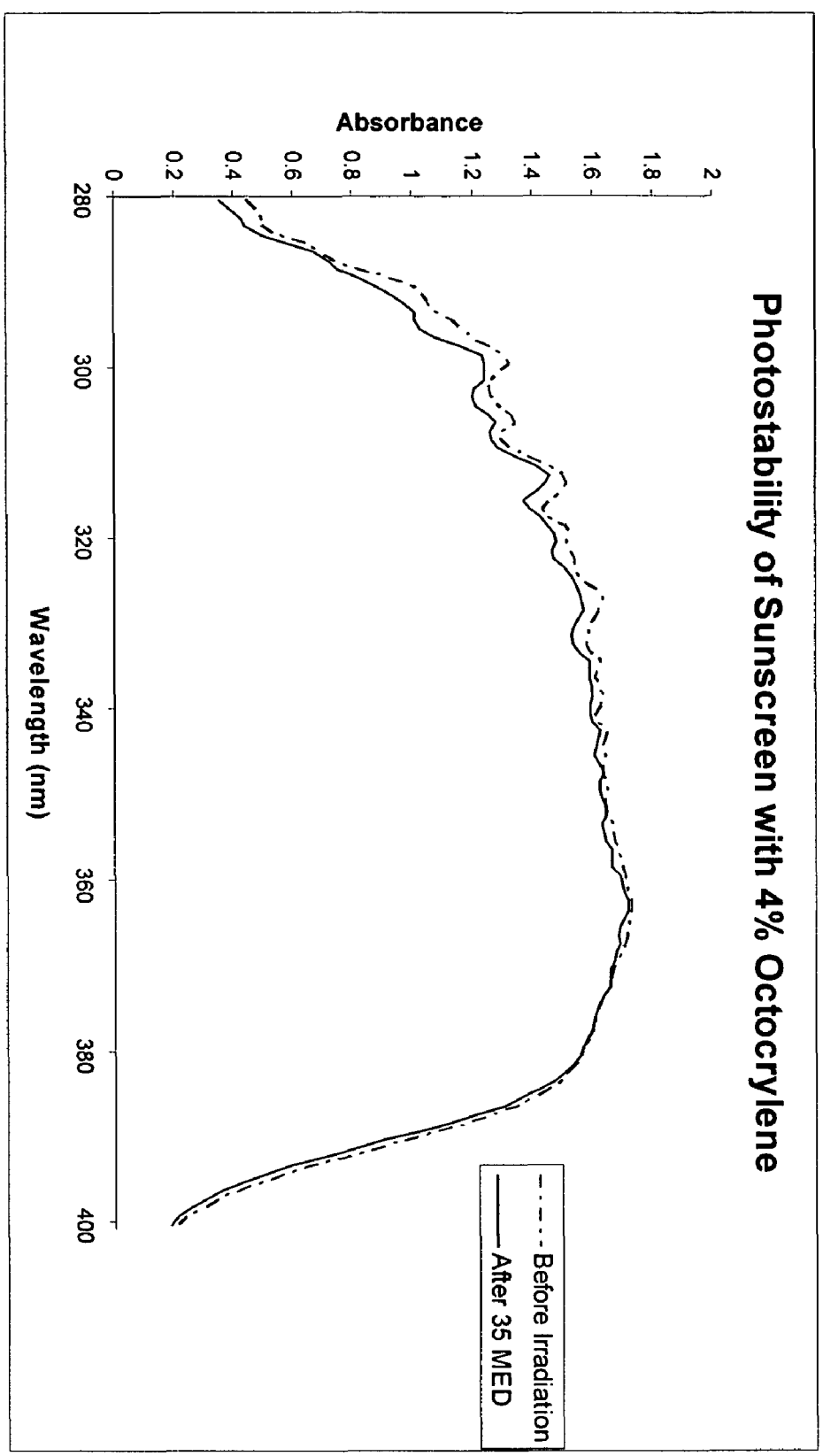
FIG. 5 is a graph of the absorbance of a sunscreen composition that includes 4% by weight octocrylene and 3% by weight avobenzone before and after irradiation of 35 MED of UV light having a wavelength of 280 nm to 400 nm.

FIGS. 3, 4 and 5 show the photostability of a sunscreen composition that includes isopropyl naphthylphenyl cyanoacrylate (FIG. 3), benzophenone-3 (FIG. 4) and octocrylene (FIG. 5). Photostability is assessed by measuring the absorbance on a Labsphere UV-1000S Ultraviolet Transmittance Analyzer (softer version 1.27) before and after irradiation with a Solar Light Company model 16S solar simulator (equipped with a WG 320 filter to transmit radiation greater than 290 nm). The radiation dose used was 35 MED. Output was monitored by a PMA 2105 UV-B DCS Detector (biologically weighted) and controlled by a PMA 2100 Automatic Dose Controller (Solar Light Co.). A slide is prepared with the sunscreen composition of interest.

To test stability, a slide is positioned on the UV transmittance analyzer using registration marks, and a scan of a 1 cm spot on the slide is performed. The slide is prepared with a synthetic skin substrate used for testing sunscreen compositions (VITRO-SKIN substrate by IMS, Inc. of Milford, Conn.). To prepare the substrate, a 300 g solution of 18 wt % glycerin and 82 wt % deionized water was added to a hydrating chamber (IMS), and a sheet of VITRO-SKIN was placed in the hydrating chamber and left overnight (approximately 16 hours). Several 6.5 cm squares were cut from the hydrated VITRO-SKIN and these squares were used for absorbance measurements.

To prepare the slide for testing, a minimum 100 µl of sunscreen composition is drawn or placed into a pipet tip (Justor 1100 DG, set to dispense 100 µl). Using steady, even pressure on the pipette plunger, the test substance was applied to VITRO-SKIN square in a pattern of at least 50 small dots arranged to cover a 6 cm center of a square. The VITRO-SKIN square was then placed on a foam block, and the test material was spread by finger (covered with a latex glove or finger cot), first in a circular motion, then by a side-to-side motion during which the VITRO-SKIN is deformed by the pressure. The square was then mounted in a slide holder (60 mm×60 mm glassless slide mounts with metal masks by Gepe Management AG, Zug, Switzerland) and allowed to dry for 30-60 minutes.

To test stability of a slide in the UV-B range, the slide was positioned on the UV transmittance analyzer using registration marks, and a scan of a 1 cm spot on the slide was performed. The slide was then transferred to a holder placed adjacent to the solar simulator and, using a calipers, was positioned such that the beam of UV radiation exiting the solar simulator illuminated the same 1 cm spot on the slide. To test stability of a slide in the UV-A range, a WG335 filter was installed in the beam path. The following software settings were used: UV-B=290-320 nm; UV-A=320-400 nm. Following an exposure of 35 MED for the UV-B studies and 120 J/cm$^2$ for the UV-A studies, the slide was again placed in position on the UV transmittance analyzer, and a scan of the exposed spot was performed.

FIG. 3 is a graph of the absorbance of the first sunscreen composition listed in Table II, before and after exposure to 35 MED irradiation. As seen in FIG. 3, the sunscreen composition containing 4% isopropyl naphthylphenyl cyanoacrylate and 3% avobenzone maintained its absorbance characteristics after 35 MED irradiation.

FIG. 4 is a graph of the absorbance of the second sunscreen composition listed in Table II, before and after exposure to 35 MED irradiation. As seen in FIG. 4, the sunscreen composition including 4% benzophenone-3 and 3% avobenzone maintains its absorbance properties after irradiation of 35 MED.

FIG. 5 is a graph of the absorbance of the third sunscreen composition listed in Table II, before and after exposure to 35 MED irradiation. As seen in FIG. 5, the sunscreen composition including 4% octocrylene and 3% avobenzone maintains its absorbance properties after irradiation of 35 MED.

Example 3

A determination of the Sun Protection Factor (SPF) of the sunscreen compositions listed in Table II was performed. To test the SPF of the compositions, each slide is placed on the UV transmittance analyzer and scans are taken from five locations on the slide. An SPF report was generated for each slide using the Labsphere software UV1000S, Version 1.27.

The results of the SPF testing for the composition listed in Table II are shown below in Table III:

TABLE III

| Composition | | SPF Results |
|---|---|---|
| Composition with 4% | Scan No. 1 | 23.92 |
| Isopropyl α-cyano-β,β- | Scan No. 2 | 22.89 |
| naphthylphenyl acrylate | Scan No. 3 | 24.99 |
| (Table II) | Scan No. 4 | 25.87 |
| | Scan No. 5 | 25.42 |
| | Average SPF | 24.6 |
| Composition with 4% | Scan No. 1 | 21.74 |
| Benzophenone-3 | Scan No. 2 | 26.59 |
| (Table II) | Scan No. 3 | 21.77 |
| | Scan No. 4 | 24.23 |
| | Scan No. 5 | 23.70 |
| | Average SPF | 23.6 |
| Composition with 4% | Scan No. 1 | 23.65 |
| Octocrylene | Scan No. 2 | 23.55 |
| (Table II) | Scan No. 3 | 23.18 |
| | Scan No. 4 | 24.38 |
| | Scan No. 5 | 25.49 |
| | Average SPF | 24.0 |

The results shown above in Table III indicate that the addition of 4% isopropyl α-naphthylphenyl cyanoacrylate to a topical composition provides an SPF of about 24.6, which is comparable to the known and commercially used additives of benzophenone-3 and octocrylene.

The foregoing description is given for clearness of understanding only, and no unnecessary limitations should be understood therefrom, as modifications within the scope of the compounds, compositions, and methods described herein may be apparent to those having ordinary skill in the art.

What is claimed is:

1. A method of absorbing ultraviolet radiation having a wavelength in the range of about 320 nm to about 400 nm and photostabilizing a dibenzoylmethane derivative, comprising the step of adding a photostabilizing amount of a compound of formula (I) to a composition comprising a dibenzoylmethane derivative:

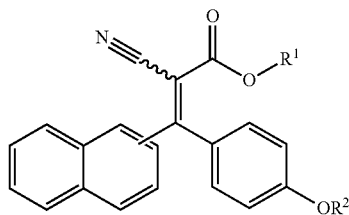
(I)

wherein $R^1$ is $C_1$-$C_{50}$ alkyl; $R^2$ is a $C_1$-$C_{50}$ alkyl and
exposing said composition to ultraviolet radiation having a wavelength in the range of about 320 nm to about 400 nm.

2. The method of claim 1, wherein said dibenzoylmethane derivative is selected from the group consisting of 2-methyldibenzoylmethane; 4-methyldibenzoylmethane; 4-isopropyldibenzoylmethane; 4-tert-butyldibenzoylmethane; 2,4-dimethyldibenzoylmethane; 2,5-dimethyldibenzoylmethane; 4,4'-diisopropyldibenzoylmethane; 4,4'-dimethoxydibenzoylmethane; 4-tert-butyl-4'-methoxydibenzoylmethane; 2-methyl-5-isopropyl-4'-methoxydibenzoylmethane; 2-methyl-5-tert-butyl-4'-methoxydibenzoylmethane; 2,4-dimethyl-4'-methoxydibenzoylmethane; 2,6-dimethyl-4-tert-butyl-4'-methoxydibenzoylmethane, and combinations thereof.

3. A method of protecting a surface from ultraviolet radiation having a wavelength in the range of about 320 nm to about 400 nm comprising topically applying to said surface, in an acceptable carrier, a composition comprising a dibenzoylmethane derivative and a compound of formula (I):

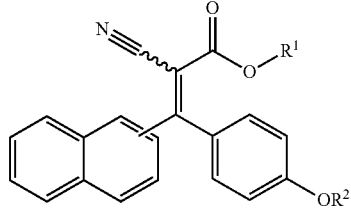
(I)

wherein $R^1$ is $C_1$-$C_{50}$ alkyl; $R^2$ is a $C_1$-$C_{50}$ alkyl and
exposing said composition to ultraviolet radiation having a wavelength in the range of about 320 nm to about 400 nm.

4. The method of claim 3, wherein said surface is human skin and said carrier is a cosmetically acceptable carrier.

5. A method of absorbing ultraviolet radiation having a wavelength in the range of about 320 nm to about 400 nm and photostabilizing a dibenzoylmethane derivative, comprising the step of adding a photostabilizing amount of a compound of formula (I) to a composition comprising a dibenzoylmethane derivative:

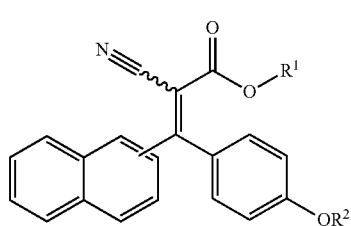
(I)

wherein $R^1$ is $C_1$-$C_{50}$ alkyl; $R^2$ is a $C_1$-$C_{50}$ alkyl and
exposing said composition to ultraviolet radiation having a wavelength in the range of about 320 nm to about 400 nm, wherein said compound of formula (I) exhibits a greater absorbance of ultraviolet radiation having a wavelength in the range of about 320 nm to about 400 nm than ultraviolet radiation having a wavelength in the range of about 290 nm to about 320 nm.

* * * * *

UNITED STATES PATENT AND TRADEMARK OFFICE
CERTIFICATE OF CORRECTION

| | | |
|---|---|---|
| PATENT NO. | : 8,158,678 B2 | Page 1 of 1 |
| APPLICATION NO. | : 11/101214 | |
| DATED | : April 17, 2012 | |
| INVENTOR(S) | : Craig A. Bonda et al. | |

It is certified that error appears in the above-identified patent and that said Letters Patent is hereby corrected as shown below:

On the Title Page:

At field (73), "CPH Innovations Corp." should be --Hallstar Innovations Corp.--.

Signed and Sealed this
Third Day of July, 2012

David J. Kappos
*Director of the United States Patent and Trademark Office*